(12) United States Patent
Yee

(10) Patent No.: US 9,265,656 B2
(45) Date of Patent: Feb. 23, 2016

(54) GRID PATTERN LASER TREATMENT AND METHODS FOR TREATING AN EYE

(71) Applicant: Iridex Corporation, Mountain View, CA (US)

(72) Inventor: Kingman Yee, San Jose, CA (US)

(73) Assignee: IRIDEX Corporation, Mountain View, CA (US)

( * ) Notice: Subject to any disclaimer, the term of this patent is extended or adjusted under 35 U.S.C. 154(b) by 435 days.

(21) Appl. No.: 13/655,763

(22) Filed: Oct. 19, 2012

(65) Prior Publication Data

US 2013/0116672 A1 May 9, 2013

Related U.S. Application Data

(60) Provisional application No. 61/549,036, filed on Oct. 19, 2011.

(51) Int. Cl.
*A61B 19/00* (2006.01)
*A61F 9/008* (2006.01)

(52) U.S. Cl.
CPC .............. *A61F 9/00821* (2013.01); *A61F 9/008* (2013.01); *A61F 2009/00863* (2013.01)

(58) Field of Classification Search
CPC ..... A61F 9/007; A61F 9/008; A61F 9/00802; A61F 9/00821; A61F 9/00825; A61F 2009/00861; A61F 2009/00863; A61B 18/20
USPC ............ 606/3–6, 10–12; 607/88–92; 128/898
See application file for complete search history.

(56) References Cited

U.S. PATENT DOCUMENTS

| 5,085,492 | A | 2/1992 | Kelsoe et al. |
| 7,766,903 | B2 * | 8/2010 | Blumenkranz ......... A61F 9/008 606/10 |
| 7,771,417 | B2 | 8/2010 | Telfari et al. |

(Continued)

FOREIGN PATENT DOCUMENTS

| JP | 4349705 | 7/2009 |
| JP | 4377405 | 9/2009 |

(Continued)

OTHER PUBLICATIONS

Office Action for 13656332, Final Rejection 04072015.*

(Continued)

*Primary Examiner* — Ahmed Farah
(74) *Attorney, Agent, or Firm* — Kilpatrick Townsend and Stockton LLP

(57) ABSTRACT

Embodiments of the invention provide systems and methods for treating the retina and/or other areas of a patient's eye. The procedures may involve using one or more treatment beams (e.g., lasers) to cause photocoagulation or laser coagulation to finely cauterize ocular blood vessels and/or prevent blood vessel growth to induce one or more therapeutic benefits. In other embodiments, a series of short duration light pulses (e.g., between 5-15 microseconds) may be delivered to the retinal tissue with a thermal relaxation time delay between the pulse to limit the temperature rise of the target retinal tissue and thereby limit a thermal effect to only the retinal pigment epithelial layer. Such procedures may be used to treat diabetic retinopathy, macular edema, and/or other conditions of the eye. The treatment beam may be delivered within a treatment boundary or pattern defined on the retina of the patient's eye.

19 Claims, 11 Drawing Sheets

(56) References Cited

U.S. PATENT DOCUMENTS

| | | |
|---|---|---|
| 8,363,783 B2 | 1/2013 | Gertner et al. |
| 8,366,704 B2 * | 2/2013 | Lin et al. ............ 606/10 |
| 8,409,180 B2 | 4/2013 | Blumenkranz et al. |
| 8,734,433 B2 * | 5/2014 | Palanker et al. ........... 606/4 |
| 2001/0046132 A1 | 11/2001 | Lanzetta et al. |
| 2002/0051116 A1 | 5/2002 | Van Saarloos et al. |
| 2004/0170304 A1 | 9/2004 | Haven et al. |
| 2006/0083466 A1 | 4/2006 | Boutoussov |
| 2006/0100677 A1 * | 5/2006 | Blumenkranz et al. ......... 607/89 |
| 2007/0121069 A1 * | 5/2007 | Andersen et al. ............ 351/221 |
| 2007/0129775 A1 * | 6/2007 | Mordaunt et al. ............. 607/88 |
| 2007/0185475 A1 | 8/2007 | Frey et al. |
| 2010/0004643 A1 | 1/2010 | Frey et al. |
| 2012/0296320 A1 * | 11/2012 | Lin et al. ........... 606/4 |
| 2013/0110092 A1 * | 5/2013 | Yee ............ A61F 9/00821 606/4 |
| 2013/0110093 A1 * | 5/2013 | Yee ............ A61F 9/00821 606/4 |
| 2013/0110206 A1 * | 5/2013 | Yee ............ A61F 9/00821 607/89 |
| 2013/0116672 A1 | 5/2013 | Yee |
| 2013/0317570 A1 * | 11/2013 | Luttrull et al. ............. 607/89 |
| 2014/0228824 A1 * | 8/2014 | Yee ............ A61F 9/00821 606/4 |

FOREIGN PATENT DOCUMENTS

| | | |
|---|---|---|
| JP | 2011-156290 | 8/2011 |
| JP | 2011-212349 | 10/2011 |
| JP | 2011-212352 | 10/2011 |
| JP | 2011-224345 | 11/2011 |
| JP | 2011-234742 | 11/2011 |
| JP | 5066094 | 8/2012 |
| JP | 5091149 | 9/2012 |

OTHER PUBLICATIONS

International Search Report and Written Opinion of PCT/US2012/060979, mailed Mar. 1, 2013, 16 pages.

* cited by examiner

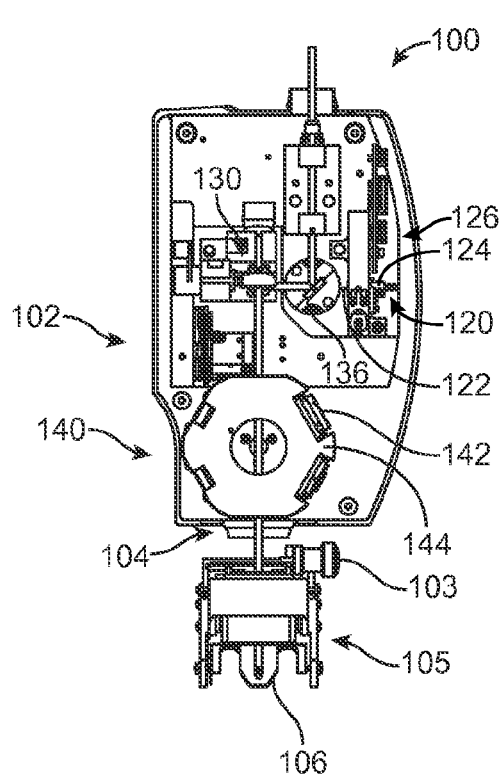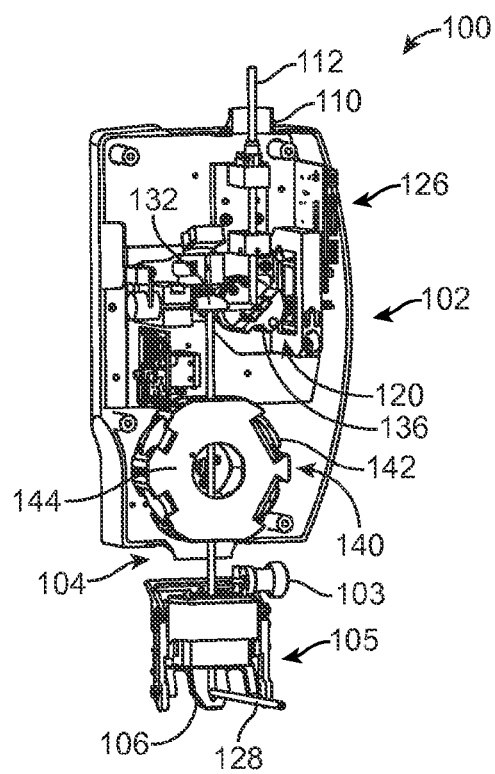
FIG. 1D          FIG. 1E
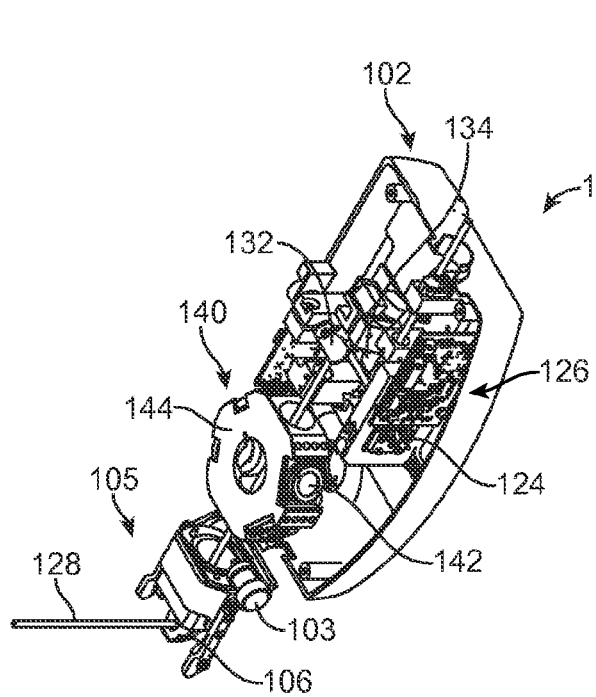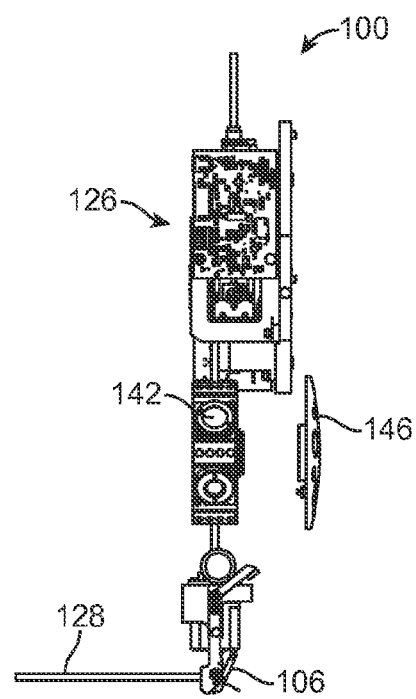
FIG. 1F          FIG. 1G

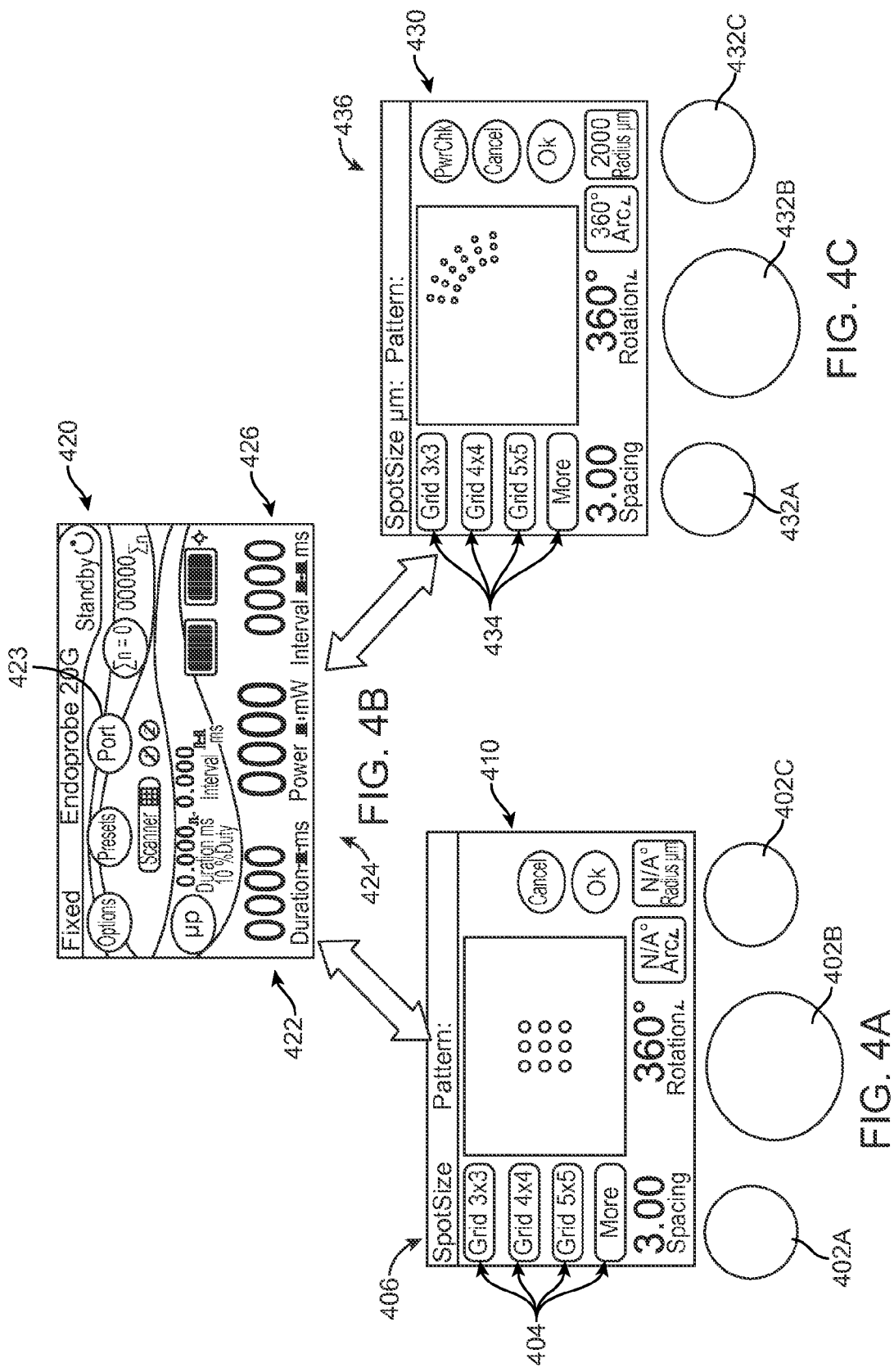

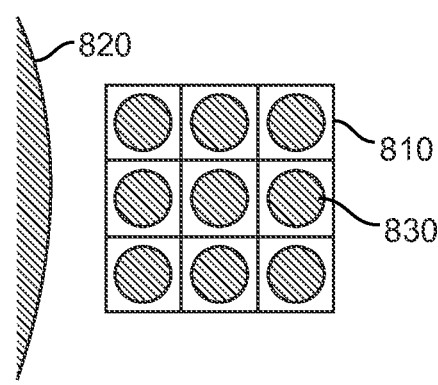
FIG. 8
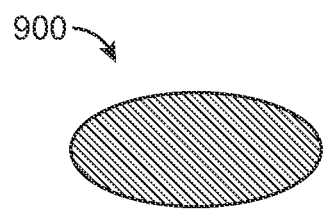
FIG. 9A
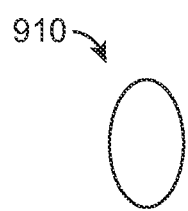 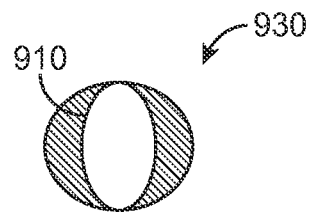
FIG. 9B          FIG. 9C

GRID PATTERN LASER TREATMENT AND METHODS FOR TREATING AN EYE

CROSS-REFERENCES TO RELATED APPLICATIONS

This application claims priority to Provisional U.S. Patent Application No. 61/549,036 filed Oct. 19, 2011, entitled "Grid Pattern Therapeutic Treatment," the entire disclosure of which is hereby incorporated by reference, for all purposes, as if fully set forth herein.

BACKGROUND

Therapeutic lasers are often used to treat various conditions of the eye. For example, a specific type of condition that may be treated with such lasers is diabetic retinopathy. Diabetic retinopathy, is damage to the retina that is due to complications of diabetes. If left untreated, diabetic retinopathy can eventually lead to blindness. Diabetic retinopathy typically results from microvascular retinal changes. For example, diabetic induced effects may damage tissue of the eye, which may change the formation of the blood-retinal barrier and make the retinal blood vessels become more permeable. In treating such conditions, one or more light beams may be directed into the eye and/or onto retinal tissue to cause photocoagulation of the tissue so as to finely cauterize ocular blood vessels and/or prevent blood vessel growth to induce various therapeutic benefits. Laser photocoagulation is commonly used for early stages of retinopathy.

In providing laser photocoagulation treatments, however, it is important to avoid damaging sensitive tissue of the eye, such as the fovea, macula, and the like. In certain instances, it may be desired to treat tissue close to one or more of these areas while ensuring that damage to such areas is avoided. Conventional laser photocoagulation techniques do not offer optimal solutions to treating areas close to such sensitive tissue while ensuring that damage to such tissue will be avoided or greatly reduced. Accordingly, there is a need in the art for improved laser photocoagulation methods for treating various conditions of the eye, such as diabetic retinopathy.

SUMMARY OF THE INVENTION

Embodiments of the invention described herein provide systems and methods for treating retina tissue and/or other areas of a patient's eye. The procedures may involve using one or more light beams (e.g., lasers) to cause photocoagulation to finely cauterize ocular blood vessels and/or prevent blood vessel growth to induce one or more therapeutic benefits. Such procedures may be used to treat diabetic retinopathy, macular edema, and/or other conditions of the eye. According to one aspect, a method for treating an eye of a patient is provided. The method may include projecting a first beam onto retinal tissue of the patient's eye. A boundary separating the retinal tissue to a first area and a second area may be defined on the retinal tissue via the first beam. A therapeutic treatment may be delivered via a second beam to the retinal tissue of the patient's eye by selectively directing the second beam onto the retinal tissue of the patient's eye within the first area.

According to one embodiment, the method may also include positioning the boundary adjacent an identified region of the patient's eye so that the identified region is within the second area. The identified region may include or define tissue that is not to be treated with the treatment. The second beam may be directed within the first area so as to avoid delivering the therapeutic treatment to the tissue of the identified region. The boundary may include a pattern of geometric shapes that each define an area within which the second beam is to be directed to deliver the treatment, and the second beam may be directed within each of the geometric shapes.

The pattern of geometric shapes may be defined on the retinal tissue of the eye by controlling (e.g., via a scanning device) a location of the first beam on the retinal tissue such that the first beam outlines the pattern of geometric shapes on the retinal tissue. The location of the first beam may be adjusted between each of a plurality of pulses. The pattern of geometric shapes may include: a grid having a plurality of squares, a grid having a plurality of rectangles, a semicircle pattern, a pattern of circles, a hexagonal pattern, and the like. The second beam may be directed over a geometric center of each of the geometric shapes. A spot of the second beam that is incident on the retinal tissue may be entirely within a periphery of the geometric shape formed by the first beam.

According to some embodiments, the first beam may not be delivered when a pulse of the second beam is delivered and vice versa. According to some embodiment, a plurality of pulses of the second beam may be delivered within the boundary to provide the treatment. According to some embodiments, a scale of the boundary or an orientation of the boundary or both may be adjusted prior to or simultaneously with providing the therapeutic laser treatment. According to some embodiments, defining the boundary may include directing the first beam along a periphery of the boundary. The first beam may have a visible spot size on the retina that is smaller than a spot size of the second beam. Delivering the therapeutic treatment may include causing photocoagulation of the retinal tissue. According to some embodiments, the second beam may be delivered in a series of pulses of sufficiently short duration so as to avoid inducing traditional photocoagulation of the retinal tissue while inducing photoactivation of a therapeutic healing response.

According to another embodiment, a method for providing therapeutic treatment to a patient's eye is provided. The method may include projecting a treatment pattern onto a retina of the patient's eye. The treatment pattern may define a first area of retinal tissue and a second area of retinal tissue. A therapeutic treatment may be delivered (e.g., via a treatment beam) to retinal tissue of the first area by selectively directing the treatment beam within the first area.

According to some embodiments, the treatment pattern may include a pattern of geometric shapes and each geometric shape may define a treatment area within which the treatment beam is to be directed. The treatment beam may be sequentially directed within each of the geometric shapes. The treatment pattern may include or define a grid having a plurality of rows and columns. The treatment beam may be sequentially scanned along, and preferably within, the plurality of rows and columns to deliver the treatment beam to the retinal tissue, preferably within or near a geometric center of each of the geometric shapes.

The grid may include an M×N array of squares or rectangles arranged in a linear or semicircular pattern. According to some embodiments, the method may also include projecting a second treatment pattern onto the retina at a location that has not received the treatment. The second treatment pattern may define a third area of retinal tissue and a fourth area of retinal tissue. The therapeutic treatment may be delivered to retinal tissue of the third area by selectively directing the treatment beam within the third area.

According to another aspect, a system for providing a therapeutic treatment to a patient's eye is provided. Among other things, the system may include: a first beam source, a second beam source, an aiming device, and a processor. The first beam source may be configured to transmit a first beam along a first beam path. The second beam source may be configured to transmit a second beam along a second beam path. The aiming device may be disposed along the first and second beam paths and configured to scan the first beam and the second beam along a retina of the patient's eye. The processor may be coupled to the aiming device and configured to: define, via the first beam, a treatment boundary separating a region of the retina into a first area and a second area, and direct the second beam onto the retina within the first area defined by the first beam so as to deliver the therapeutic treatment to the retinal tissue of the patient's eye.

BRIEF DESCRIPTION OF THE DRAWINGS

The present invention is described in conjunction with the appended figures:

FIGS. 1A-1G illustrate various perspective views of an adapter that may be coupled with an ophthalmic imaging instrument to enable the ophthalmic imaging instrument to provide a boundary defined therapeutic treatment.

FIGS. 4A-4C illustrate block diagrams of a display interface that may be used with the system of FIG. 3.

FIG. 8 illustrates a treatment pattern being positioned adjacent a feature or tissue of a patient's retina.

FIGS. 9A-9C illustrate an oblong or oval cross sectional profile of a treatment laser that may be used to compensate for continuous movement of the treatment laser during a treatment procedure.

Figure 1A:
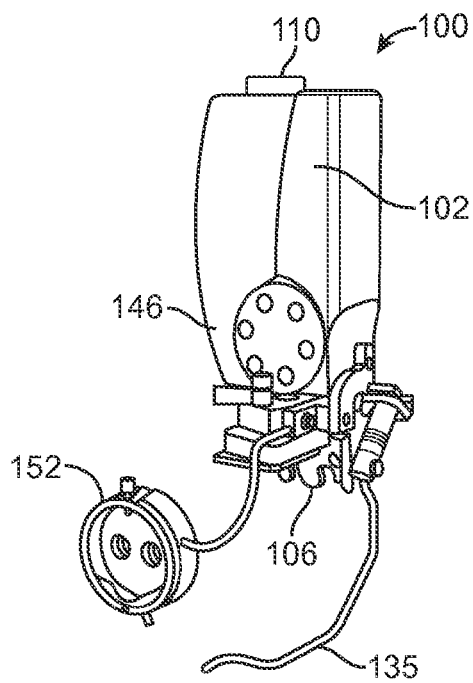

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It should be understood that various changes may be made in the function and arrangement of elements without departing from the spirit and scope of the invention as set forth in the appended claims.

Embodiments of the invention provide systems and methods for treating the retina and/or other areas of a patient's eye. The procedures may involve using one or more light beams (e.g., lasers) to cause photocoagulation to finely cauterize ocular blood vessels and/or prevent blood vessel growth to induce one or more therapeutic benefits. Such procedures may be used to treat diabetic retinopathy, macular edema, and/or other conditions of the eye. In some embodiments, photocoagulation may result in a series of visible spots that appear in the retina. In other embodiments, a series of short duration light pulses (e.g., between 5-15 microseconds) may be delivered to the retinal tissue with a thermal relaxation time delay between each pulse to limit the temperature rise of the target retinal tissue and thereby limit a thermal effect to only the retinal pigment epithelial layer. Short duration pulse treatments, such as MicroPulse™ Laser Therapy of systems and devices sold by Iridex® Corporation (hereinafter short duration pulse treatments or procedures), may not result in visible spots that appear on the retina and may result in less overall tissue damage.

The treatment light (i.e., laser light) delivered to treat and/or coagulate the retinal tissue may be delivered at therapeutic levels within a defined treatment boundary that may include a pattern of recurring geometric shapes. The treatment boundary may define an area within which treatment light at therapeutic levels is directed and outside of which treatment light is substantially not directed or is provided at sub-therapeutic levels, such as in the case of refracted light, incident light, and the like. Thus, the treatment boundary may define an area within which therapeutic treatment is provided and outside of which therapeutic treatment is not provided or minimally provided. The treatment boundary and/or pattern may be projected and/or defined on the retinal surface of the patient's eye to display the area to be treated. Because the treatment boundary may define or distinguish the area of the retina that does not receive or minimally receives the therapeutic treatment, a peripheral edge of the treatment boundary may be positioned adjacent sensitive tissue of the retina and/or anywhere that the therapeutic treatment is not desired to ensure that the sensitive tissue or area will not receive or will minimally receive the therapeutic treatment. It should be realized that some therapeutic light may be incident upon tissue outside of the treatment boundary due to refraction, light scattering, and the like, but such light will be minimal and likely have minimal effect upon the tissue outside of the treatment boundary. Thus, embodiments of the invention provide precise controls for determining areas of the retina that will receive therapeutic treatment and areas that will not.

The peripheral edge of the treatment boundary, along with the remainder of the treatment boundary, may be defined and displayed on a user interface, map or image of the retina, and/or on the retina itself so that a physician or user providing the therapeutic treatment is aware of the outer boundary of the treatment area. Since the outer boundary of the treatment area is displayed, the physician may closely abut or place the treatment area proximate to sensitive tissue and/or to any other area while ensuring that the sensitive tissue or other area will not be treated or minimally treated.

In some embodiments, a treatment pattern includes an array of aiming spots instead of, or in addition to, an enclosed boundary or pattern. The array of aiming spots may be defined on the patient's retina as described herein and the treatment beam may be fired or delivered coaxially with respect to one or more of the aiming spots.

The treatment boundary and/or treatment pattern may be defined and/or projected on the retinal surface using one or more aiming beams. The aiming beam may be a laser beam or any other type of light beam (e.g., a beam produced by a high powered light emitting diode (LED)). The aiming beam may be generally referred to herein as an aiming laser, although it should be realized that light beams other than lasers may be used. The aiming beam may be a low intensity laserlight beam that does not damage the retinal tissue. In some embodiments, the aiming beam has a wavelength of between about 600 nm (nanometers) and about 700 nm, and more commonly about 650 nm. The aiming beam may be provided by a laser diode and may have an incident spot or cross section on the retinal tissue that is substantially smaller than an incident spot of the treatment laser that is used to treat the retinal tissue. Alternatively, in some embodiments, the aiming beam may be provided by a high powered light emitting diode (LED) in place of, or in addition to, the aiming laser. The aiming beam may be scanned on the patient's retina, or on a display interface or image of the retina, to trace or outline the treatment boundary and/or treatment pattern so as to visually display the treatment boundary and/or pattern to a physician. The treatment boundary and/or pattern defined or projected onto the retinal surface may be captured by a camera and displayed to the physician or other user on a display interface.

One or more treatment beam pulses or doses may be delivered within the treatment boundary and/or pattern to treat the retinal tissue. The treatment beam may be generally referred to herein as a treatment laser, although, like the aiming beam, it should be realized that other light beams may be used, such as a high intensity light beam from a high powered light emitting diode (LED). The treatment pulses or doses may be delivered as a scanning device continuously scans an axis of the treatment beam within the treatment boundary and/or may be delivered as the scanning device sequentially moves the treatment beam axis between specified locations within the treatment boundary. In embodiments involving treatment patterns having recurring geometric shapes, one or more treatment beam pulses may be delivered within some or each of the geometric shapes. In a specific embodiment, a single treatment beam pulse may be delivered substantially in a geometric center of each of the geometric shapes. A cross section of the incident beam light (e.g., a laser beam spot) may be roughly equivalent in size with the geometric shape. In some embodiments, the treatment beam (e.g., laser beam) may have a wavelength of between about 400 nm and 600 nm, and more commonly between about 520 nm and 560 nm.

The therapeutic treatment (also referred to herein as a boundary defined therapeutic treatment) may be provided via an adapter that is configured to be mounted onto and operate with a preexisting ophthalmic imaging instrument, such as a slit lamp. The adapter may also operate with a preexisting treatment beam source, such as a laser delivery instrument. An external controller or computer system may be communicatively coupled with the adapter and laser delivery instrument to define the treatment boundary and/or pattern on the retinal tissue and deliver the treatment beam within the treatment boundary/pattern. The adapter and/or controller may allow a preexisting slit lamp and laser delivery instrument to provide the boundary defined therapeutic treatment described herein, which slit lamp and laser delivery instrument would otherwise be incapable of delivering.

Embodiments of the invention also describe methods and system of using retinal imaging and/or tracking to provide a therapeutic treatment (e.g., the boundary defined therapeutic treatment) described herein or another therapeutic treatment. The therapeutic treatment and/or a treatment boundary may be programmed and/or documented with reference to a retinal image or model of a patient's retina. A system performing the therapeutic treatment may reference the retinal image or model and the programmed therapeutic treatment or treatment boundary to determine a location or area of the patient's retina to provide the therapeutic treatment. The system may then automatically begin the therapeutic treatment or display the treatment boundary/pattern and corresponding retina treatment area to a physician for review, adjustment, and/or authorization to proceed. A plurality of such therapeutic treatments may be programmed into the system so that the system may quickly and conveniently begin performing an additional therapeutic treatment shortly after completing a current or previous treatment. The provided treatments may be documented or recorded on the retinal image or model for simultaneous or subsequent review by the physician or user. For example, treatment spots or other indicia may be superimposed on the retinal image for each location or position that a pulse or dose of the treatment beam is received. The superimposed spots or indicia may document the areas of the retina for which therapeutic treatment was provided. This may be particularly useful when no visible effects of the therapeutic treatment are present on the retinal tissue, such as in short duration pulse procedures.

Referencing the therapeutic treatment and/or treatment boundary procedure with respect to the retinal image or model may also allow the system to compensate for movement of the patient's eye during the procedure. For example, retinal tracking may allow a camera to capture substantially smooth images of the retina and/or allow the system to adjust to a movement of the patient's eye and continue to deliver the therapeutic treatment at substantially the same location. Having briefly described some embodiments of the invention, additional aspects will become apparent with reference to the figures.

Embodiments of Therapeutic Treatment Hardware and Components

Figure 1B:
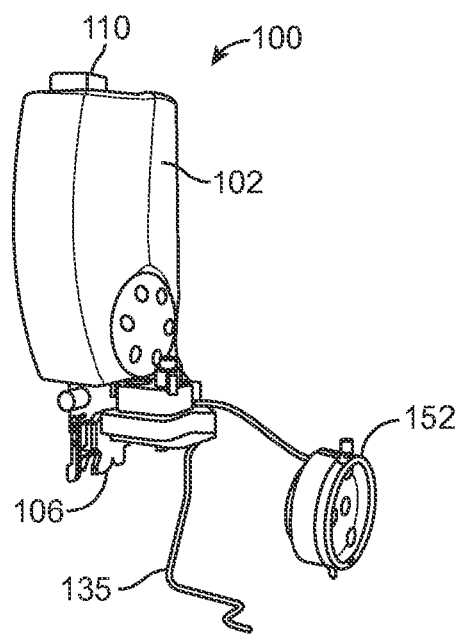
Figure 1C:
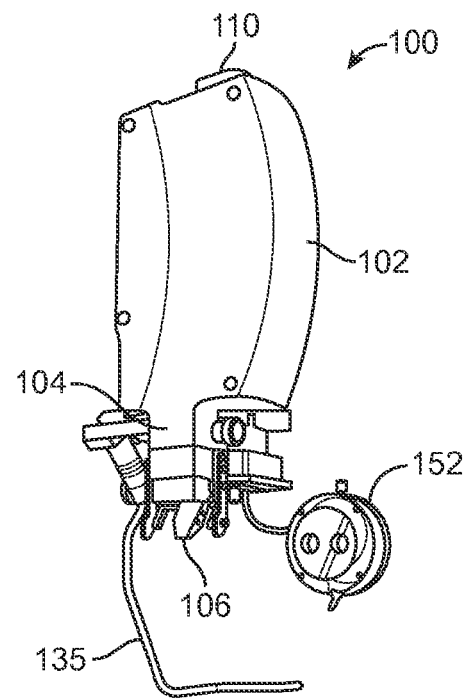
Figure 2A:
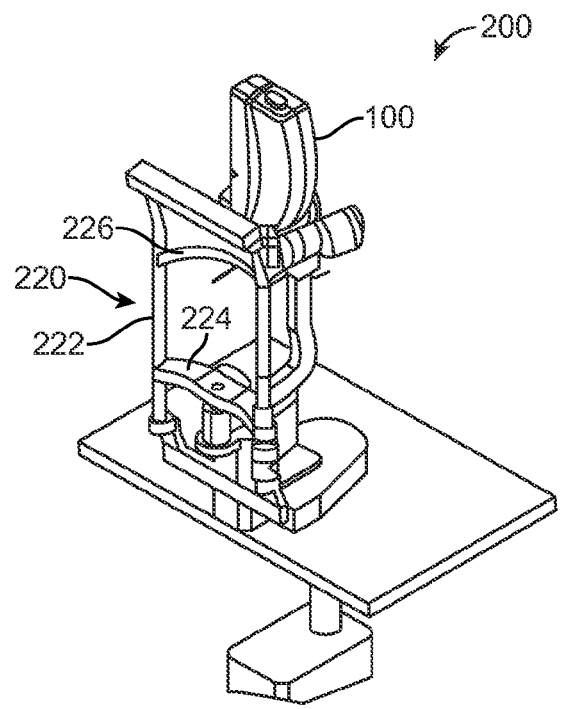
FIGS. 2A-2E illustrate various views of the adapter of FIGS. 1A-1G coupled with an ophthalmic imaging instrument.
Figure 2B:
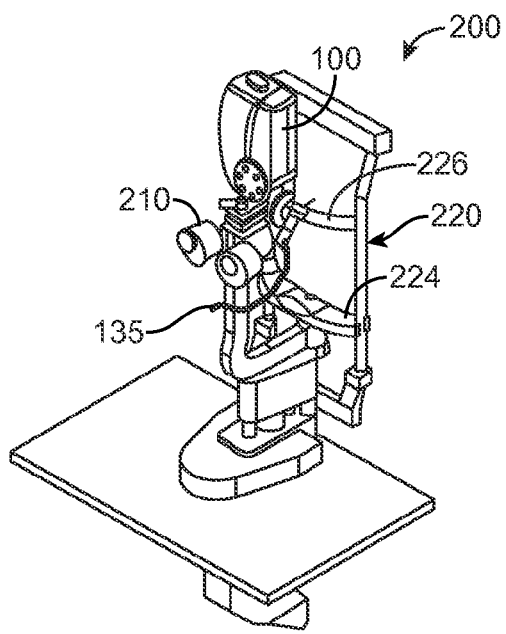
Figure 2E:
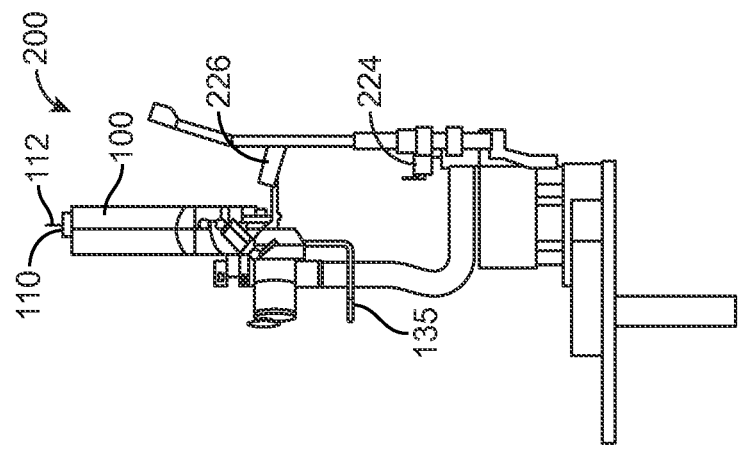
Figure 2D:
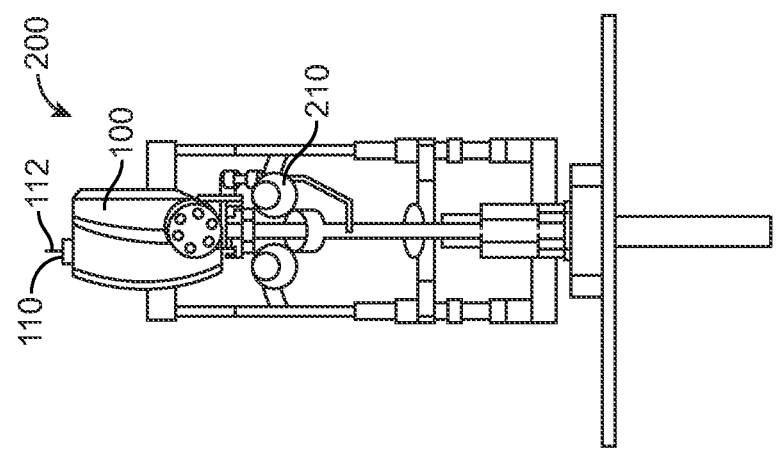
Figure 2C:
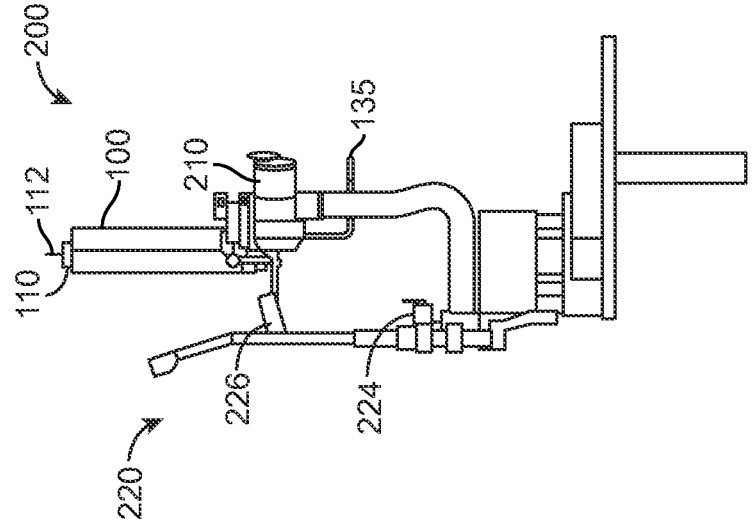

FIGS. 1A-1G illustrate perspective views of an embodiment of an adapter that may be coupled with an ophthalmic imaging instrument, such as a slit lamp, to adapt the ophthalmic imaging instrument to provide the boundary defined therapeutic treatment described herein. FIGS. 2A-2E illustrate the adapter 100 coupled with a slit lamp 200. FIGS. 1A-1C provide various perspective views of the adapter 100. FIGS. 1D-1G also provide perspective views of adapter 100 with a front cover of the adapter removed to show various components housed within adapter 100. Adapter 100 includes a housing 102 having a front and back cover coupled together. Adapter 100 also includes a mounting member 104 that releasably couples adapter 100 with the ophthalmic imaging instrument (e.g., slit lamp 200). Adapter 100 also includes adapting component 105 that facilitates in coupling adapter 100 with the ophthalmic imaging instrument 200. Component 105 may include a rotatable mounting knob 103 that presses mounting member 104 firmly against a mounting feature (not shown) of the ophthalmic imaging instrument. Component 105 also includes a mirror 106 that reflects light delivered from adapter 100 toward an eye of a patient and that may be transparent or semi-transparent so that some light is delivered back to a camera (e.g., camera 360) and/or binocular adapter 152 that couples with a binocular (e.g., binocular 210) or other eyepiece. Component 105 may further include an adjuster bar 135 that allows rotational adjustment of adapter 100 and/or the ophthalmic imaging instrument 200.

Adapter 100 further includes an interface or port 110 that couples with a fiber optic cable of an external laser delivery instrument (e.g., laser delivery instrument 310). The fiber optic cable of the external laser delivery instrument provides or delivers a treatment laser 112 to adapter 100. Adapter 100 includes mirror 136 that reflects treatment laser 112 toward an aiming device 130 (also referred to herein as a scanning device or system). Mirror 136 may be a perforated mirror, half mirror, dichroic mirror, and the like and may be mounted on a lens holder. Aiming device 130 may be a galvanometer-based scanner (commonly referred to as "galvos") manufactured by Cambridge Technology®. Aiming device 130 includes a pair of rotatable elements or mirrors, 132 and 134, mounted atop motors that rotate elements or mirrors, 132 and 134, about orthogonal axes. Each mirror, 132 and 134, may provide 1-D beam deflection, so that the pair of mirrors provides 2-D beam deflection. Aiming device 130 is used to scan treatment laser 112 and/or other lasers (e.g., aiming laser 122) relative to the eye so that the lasers may be aimed and fired at desired locations on or within the eye. For example, aiming device 130 may be used to scan aiming laser 122 to define the treatment boundary and/or treatment pattern on retinal tissue and to scan a beam of treatment laser 112 within the treatment boundary/pattern so as to provide the boundary defined therapeutic treatment.

Aiming laser 122 passes through mirror 136 to aiming device 130. In some embodiments, adapter 100 may include another interface or port (not shown) that receives the aiming laser 122 from an external laser delivery instrument or source (not shown), which may be the same laser delivery instrument that delivers treatment laser 112 or a different unit. In other embodiments, adapter 100 includes a laser delivery instrument or source 120 within housing 102. For example, laser delivery instrument 120 may include a laser diode 124, or alternatively a high powered LED, that provides the aiming laser 122. Laser delivery instrument 120 may also include a computing device 126, such as a memory device and/or processor, that is communicatively coupled with an external controller (e.g., controller 330 and/or 310) to control the delivery of aiming laser 122.

In one embodiment, aiming laser 122 may be provided along a laser path substantially orthogonal to a laser path of treatment laser 112. The laser paths of aiming laser 122 and treatment laser 112, however, may be aligned or substantially coaxial after aiming laser 122 pass through mirror 136. For example, laser path 128 illustrates a path of a laser being delivered from aiming device 130 and reflected off mirror 106 toward an eye of a patient. Laser path 128 may correspond to either or both aiming laser 122 and treatment laser 112 since at this point the laser paths may be coaxially aligned.

Aiming laser 122 may have a wavelength selected within the visible spectrum to provide improved visibility of the treatment boundary and/or pattern on the retina. For example, in some embodiments, aiming laser 122 has a wavelength between about 600 nm and about 700 nm, and more commonly about 650 nm. Aiming laser 122 may be a low intensity beam that does not damage retinal and/or other tissue of the eye. Aiming laser 122 may also have an incident spot or cross section that is substantially smaller than an incident spot of treatment laser 112. In some embodiments, treatment laser 112 may also have a wavelength selected within the visible spectrum, although non-visible wavelengths may also be used. In a specific embodiment, treatment laser 112 has a wavelength of between about 400 nm and 600 nm, and more commonly between about 520 nm and 560 nm. Treatment laser 112 may be used to coagulate retinal and/or other tissue of the eye and/or provide other therapeutic healing.

Adapter 100 also include a magnification mechanism 140 that may be used to increase the cross section or incident spot of the treatment laser 112 and/or aiming laser 122. Magnification mechanism 140 is positioned along a laser path (e.g., laser path 128) distally of aiming device 130. Magnification mechanism 140 includes a plurality of lenses 142 mounted on a rotatable lens holder 144. Each lens has a specified optic power that increases or decreases the cross section or incident spot of the treatment laser 112 and/or aiming laser 122. Lens holder 144 may be rotated so that a desired lens is positioned along laser path 128. In some embodiments, lens holder 144 is rotated by rotating a control knob 146 positioned on an exterior surface of housing 102, although in some embodiments, lens holder 144 may be rotated electronically.

FIGS. 2A-2E illustrate various perspective views of adapter 100 mounted with slit lamp 200, which may be any slit lamp commonly used, such as those manufactured by Haag-Streit International®, Carl Zeiss®, and the like. Slit lamp 200 includes binoculars 210 that provide a stereoscopic view of the patient's eye. Binoculars 210 may be coupled with binocular adapter 152. Slit lamp 200 also includes a patient mounting frame 220 having vertical frame members 222, a chin rest 224, and head rest 226. Although not shown, slit lamp 200 may also include a joystick and foot pedal that may be used to provide functional control of various slit lamp components and/or operations and/or to deliver the therapeutic treatment beam. Slit lamp 200 and/or chin rest 224 may be vertically adjusted to accommodate patients of different size.

Figure 3:
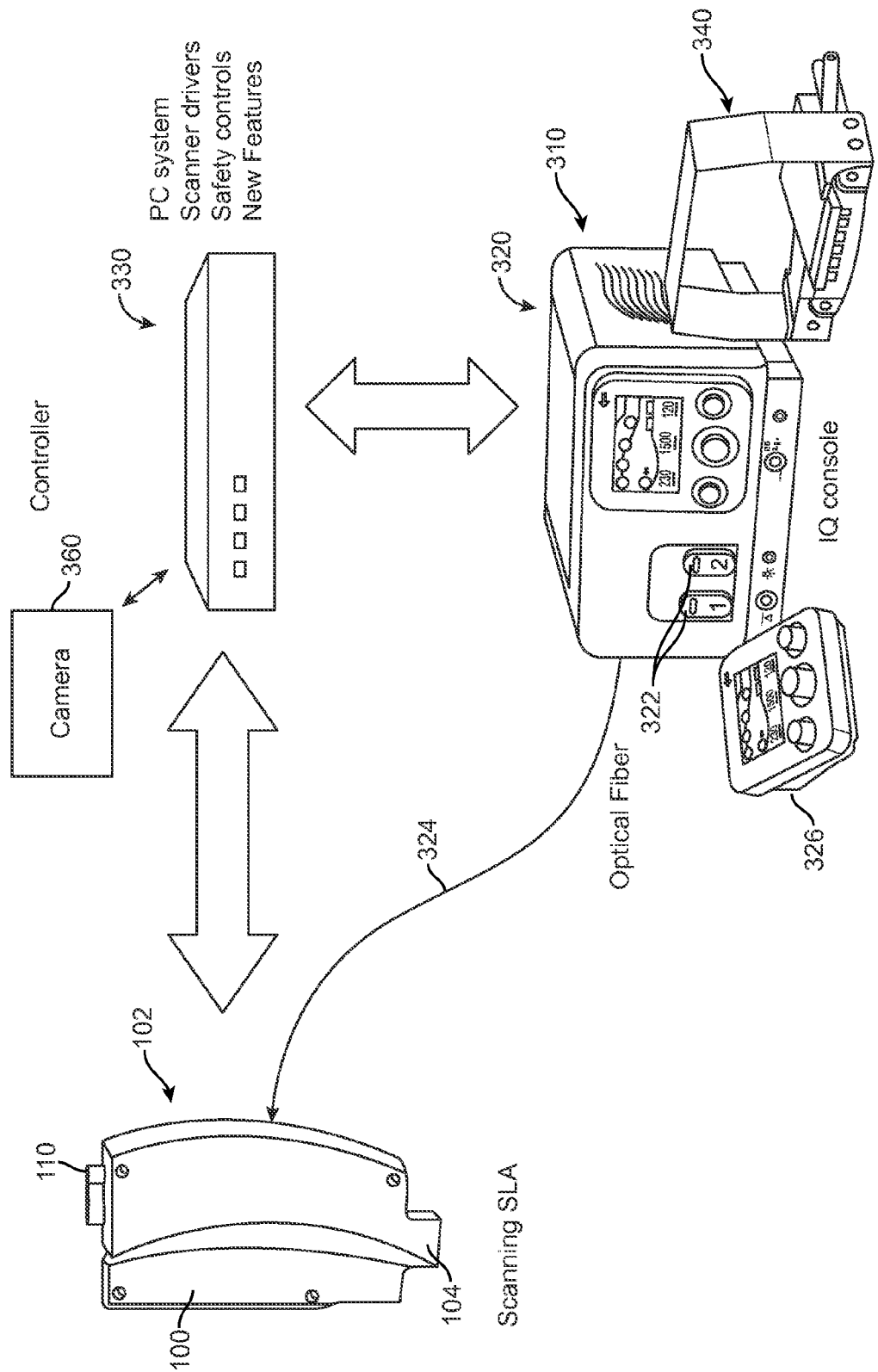
FIG. 3 illustrates a block diagram of a system for providing therapeutic treatments in accordance with an embodiment of the invention.

FIG. 3 illustrates embodiments of various controls that may be used to provide the therapeutic treatments described herein. Specifically, FIG. 3 illustrates adapter 100 coupled with an external laser delivery instrument 310 via optical fiber 324. Optical fiber 324 connects to port 110 and delivers treatment laser 112 to adapter 100. Optical fiber 324 may be coupled with one of a plurality of optical fiber ports 322 on laser delivery instrument or source 310. The optical fiber ports 322 may allow two optical fibers 324 to be connected to laser delivery instrument 310. Laser delivery instrument 310 also includes a display interface 320 (e.g., a touch screen interface) that displays settings and controls for the therapeutic treatment to be provided as shown in FIGS. 4A-4C. Laser delivery instrument 310 may also include a remote control unit 326 (wireless or wired) that allows a user to remotely operate and adjust various settings of the laser delivery instrument. Likewise, laser delivery instrument 310 may include a foot pedal 340 that is operated to perform the therapeutic treatment and/or deliver treatment laser 112. Foot pedal 340 may be wirelessly coupled with laser delivery instrument 310. Examples of laser delivery instrument 310 include the IQ 532, IQ 577, Oculight TX, and the like, manufactured by IRIDEX Corp®.

Laser delivery instrument 310 may be a conventional unit that is not able to offer the boundary defined therapeutic treatment in its conventional state. To enable the laser delivery instrument 310 to provide this treatment, a computer system 330 may be communicatively coupled with laser delivery instrument 310 and/or adapter 100. Computer system 330 may be a separate set top box that plugs into one or more ports of the laser delivery instrument 310 to communicate with laser delivery instrument 310. Additionally, computer system 330 may include one or more processors and memory devices that allow computer system 330 to interface with various other systems or units to perform the therapeutic treatment. Information may be routed between computer system 330 and a computer system or processor of laser delivery instrument 310 so that computer system 330 controls the delivery of treatment laser 112 and graphical displays information to a user via display interface 320. For example, computer system 330 may interface with the controls of laser delivery instrument 310 (e.g., touch screen controls, remote control 326, foot pedal 340, and the like) so that adjustment of the controls of laser delivery instrument 310 configure or adjust the settings and parameters of computer system 330. As shown in FIGS. 4A-4C, computer system 330 may control display interface 320 to display various setting and/or operations of the boundary therapeutic treatment, such as the shape, orientation, scale, geometric pattern, laser intensity and the like, of the specific treatment boundary/pattern being projected. Computer system 330 may control (via one or more instructions) laser delivery instrument 310 to delivery treatment laser 112 doses at specified points and at specified times. For example, computer system 330 may control laser delivery instrument 310 so that treatment laser 112 beams or doses are delivered within the defined treatment boundary, treatment pattern, and/or defined geometric shapes as described below. Likewise, computer system 330 may control laser delivery instrument 310 so that the delivered treatment laser 112 coagulates the retinal tissue of the eye or provides a less traumatic series of short duration pulses (e.g., short duration pulse treatments) with a defined relaxation interval between pulses as described below.

In essence, computer system 330 may be communicatively coupled with laser delivery instrument 310 so that laser delivery instrument 310 functions as a pass through input and interface device for computer system 330 to enable a physician or user to interface with computer system 330 and adjust various parameters of the therapeutic treatment. Computer system 330 also functions with the preexisting controls of laser delivery instrument 310 (e.g., foot pedal 340, internal hardware components, and the like) to deliver treatment laser 112 to adapter 100.

Computer system 330 is also communicatively coupled with adapter 100 to perform various aiming or other functions. For example, computer system 330 may control aiming or scanning device 130 and/or laser delivery instrument 120 to aim or scan treatment laser 112 and aiming laser 122 onto specified areas of the retina. Computer system 330 may interleave treatment laser 112 and aiming laser 122 during the therapeutic treatment procedure. Computing device 330 controls the delivery of aiming laser 122 and controls scanning device 130 to define or project the treatment boundary or treatment pattern onto the retina.

In some embodiments, control unit 330 switches aiming laser 122 on while treatment laser 112 is switched off to define the treatment boundary. Control unit 330 then switches aiming laser 122 off while treatment laser 112 is fired at target tissue within the treatment boundary. Between subsequent firings of treatment laser 112, control unit 330 may switch aiming laser 122 on to redefine or project the treatment boundary or pattern on the retina. As shown in FIGS. 7A-7F, the resulting visual effect to an observer may be the nearly continuous appearance of the treatment boundary or pattern on the retina while treatment spots from the treatment laser are sequentially fired and observed on target tissue within the treatment boundary or pattern. In some embodiments, such as the delivery of short duration pulses, the aiming device 130 may be continuously scanned while treatment laser 112 is fired within the treatment boundary.

Although shown as separate units, in some embodiments, laser delivery instrument 310 and computer system 330 are combined into a single unit so that substantially all the controls and operations are provided from a single unit. Further, as described in more detail below, computer system 330 may be coupled with a camera 360 (e.g., CCD camera and the like) to provide the retinal imaging and tracking features described below as well as to display the treatment boundary and/or pattern on a display device, such as display interface 320.

Computer system 330 may comprise hardware and/or software, often including one or more programmable processor units running machine readable program instructions or code for implementing some or all of one or more of the methods described herein. The code will often be embodied in a tangible media such as a memory (optionally a read only memory, a random access memory, a non-volatile memory, or the like) and/or a recording media (such as a floppy disk, a hard drive, a CD, a DVD, a memory stick, or the like).

FIGS. 4A-4C illustrate various displays that may be displayed on display interface 320. Display 410 is shown displaying a treatment pattern 406 that includes a square grid of nine treatment areas or locations within which therapeutic light will be delivered onto retinal tissue via treatment laser 112. The grid may be adjusted using controls 404 so that the grid includes a 3×3 array of treatments boxes or locations, a 4×4 array of treatment locations, a 5×5 array of treatment locations, or a user defined array of treatment locations. Display 410 also includes controls 402A-402C that may be used to set or adjust various settings, controls, and/or parameters. For example, control 402A may be used to control a spacing between center points of treatment spots that will be delivered within each of the treatment locations, or stated differently, define a scale of the treatment pattern. Control 402B may be used to control an orientation of the array of treatment locations with respect to the retina. Control 402C may be used to control an arc and/or radius of curvature of the array, if desired. FIG. 4A shows treatment pattern 406 without an arc and radius of curvature. FIG. 4C shows display 430 having an arched or curved treatment pattern 436 including three rows and six columns of treatment spots. Treatment pattern 436 includes an arc (e.g., 360°) and radius of curvature (e.g., 2000 micrometers) that are non-zero so that treatment pattern 436 is curved. Display 430 similar includes control buttons 432A-432C and 434. FIG. 4B shows a display 420 that may be used to adjust or set various parameters of the treatment laser 112 and/or aiming laser 122. For example, controls of display 420, which may include touch screen controls, may be used to adjust a duration 422 (e.g., in microsecond intervals) that the treatment laser 112 is fired, adjust a power level 424 (e.g., in microwatts) of the treatment laser 112, and adjust an interval 426 (e.g., in microseconds) between sequential treatment laser firings.

Display 420 may be used to adjust the treatment laser 112 between traditional photocoagulating procedures and short duration pulse procedures. Display 420 may also include other controls 428, such as a control that selects a port (e.g., 322) to which optic fiber 324 will connect. As described above, the controls of the display 320 may be touch screen controls or may include rotatable or selectable tabs or buttons.

Embodiments of Treatment Boundaries and/or Patterns

FIGS. 5A-5F show various embodiments of treatment boundaries and/or patterns that may be used for the therapeutic treatments described herein. These treatments boundaries/patterns may be projected or defined on the patient's retina via aiming or scanning laser 122. The projected or defined boundaries or patterns may be captured by a camera and displayed to a user or physician on a display device, such as display interface 320. The treatment boundaries/patterns define an area within which the therapeutic treatment is provided and outside of which the therapeutic treatment is not provided. One advantage of the treatment boundary process described herein is that the boundaries of the treatment area are clearly defined, which allows the physician or user to precisely know or determine where the therapeutic treatment will and will not be provided.

Figure 5A:
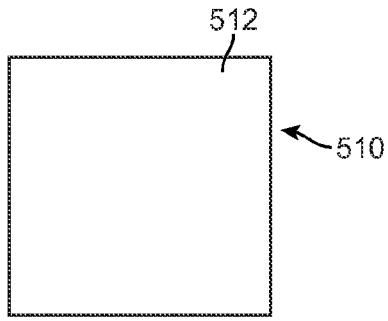
FIGS. 5A-5F illustrate various treatment boundaries and/or treatment patterns that may be used for the boundary defined therapeutic treatments.
Figure 5B:
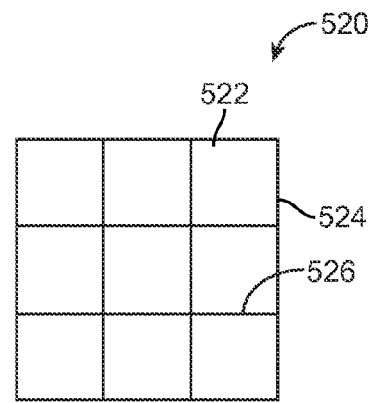
Figure 5C:
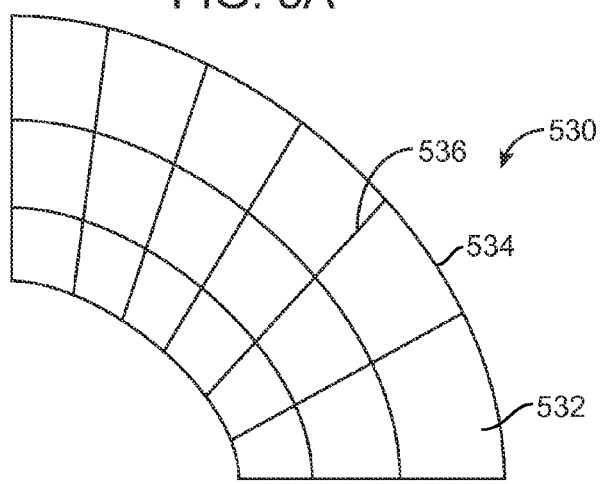
Figure 5D:
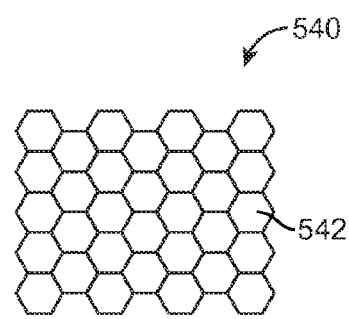
Figure 5E:
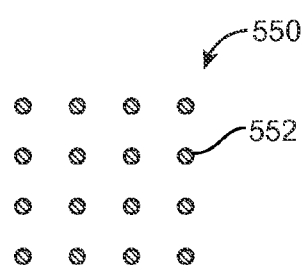
Figure 5F:
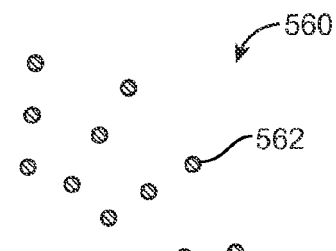

FIG. 5A shows a square or rectangular treatment boundary 510 enclosing a single treatment area 512 within which one or more treatment laser pulses or doses may be fired. FIG. 5B shows a treatment pattern 520 including a grid or array of a plurality of equally sized treatment squares or rectangles 522. Treatment pattern 520 is defined by peripheral edges 526 and internal lines 526. FIG. 5B shows a 3×3 array, although any M×N array may be used. FIG. 5C shows an arched or curved treatment pattern 530 including an array of a plurality of four sided geometric shapes 532. Each shape 532 includes opposing linear sides 536 and opposing arcuate sides 534. Treatment pattern 530 may have a radius of curvature and liner opposing sides 536 may each project radially from a center point. FIG. 5D shows a treatment pattern 540 having a plurality of hexagonal shapes 542 arranged in a honeycomb pattern. FIG. 5E shows a treatment pattern 550 having a square or rectangular array of aiming spots 552 that define locations where a treatment laser pulse or dose will be delivered. FIG. 5F shows a treatment pattern 560 having a semicircular array of aiming spots 562 that define locations where a treatment laser pulse or dose will be delivered.

The treatment boundaries, patterns, and/or geometric shapes may be projected or defined on the retina by controlling a position of the aiming laser (e.g., aiming laser 122) via scanning or aiming device, so that the aiming laser outlines or defines the treatment boundaries, patterns, and/or geometric shapes on retinal tissue and/or displays the treatment pattern on a display device or interface. The position of the aiming laser may be adjusted between each of a plurality of pulses to define or outline the treatment boundaries, patterns, and/or geometric shapes on the retina. The resulting visual effect may be a solid, semi-solid, or pulsing treatment boundary, pattern, and/or geometric shapes defined on the retina as shown in FIGS. 5A-5D.

It should be realized that FIGS. 5A-5D are for illustrative purposes only and that the treatment boundary/pattern may include various other arrays of geometric shapes, which may or may not include recurring patterns.

Figure 6A:
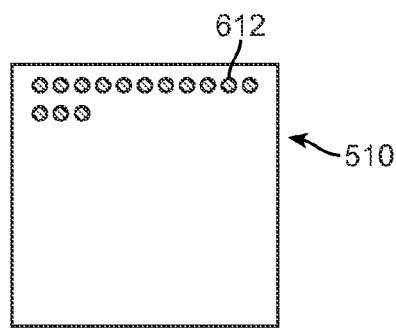
FIGS. 6A-6F illustrate laser light being delivered within or with respect to the treatment boundaries and/or treatment patterns of FIGS. 5A-5F.
Figure 6B:
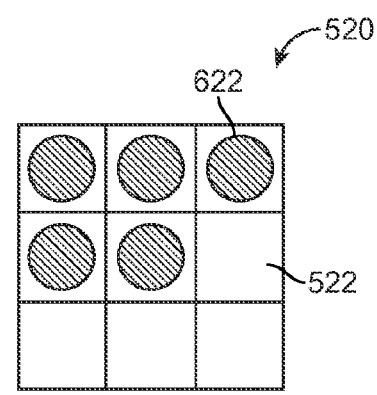
Figure 6C:
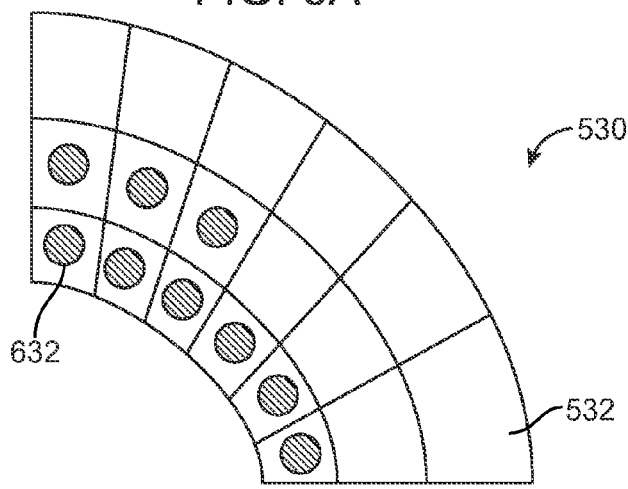
Figure 6D:
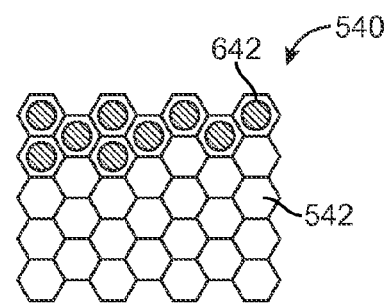
Figure 6E:
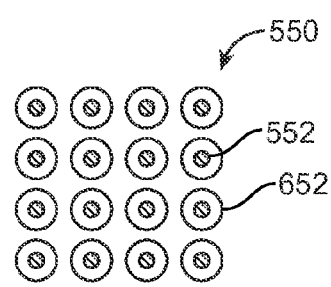
Figure 6F:
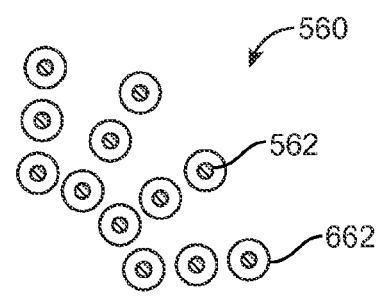
Figure 7A:
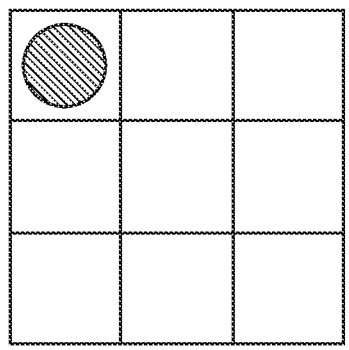
FIGS. 7A-7F illustrate a process of sequentially delivering laser light within a treatment pattern.
Figure 7B:
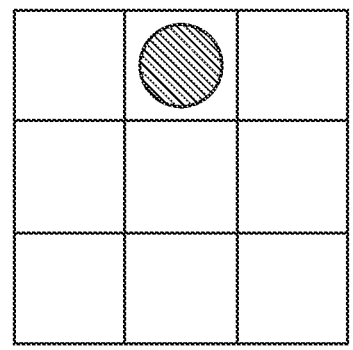
Figure 7C:
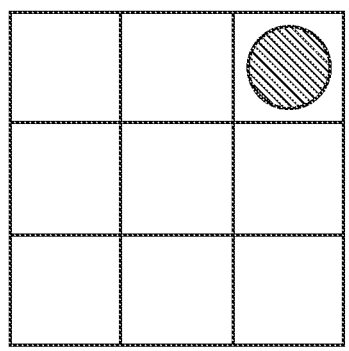
Figure 7D:
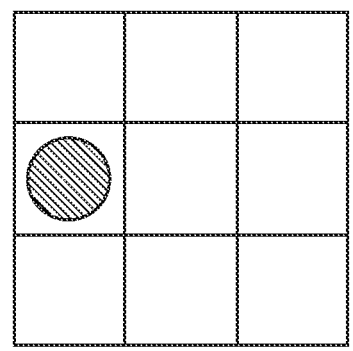
Figure 7E:
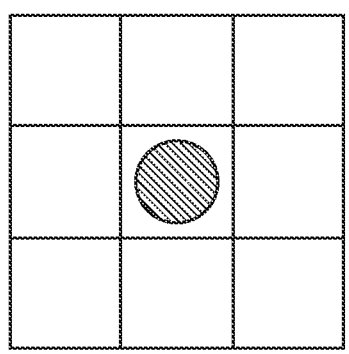
Figure 7F:
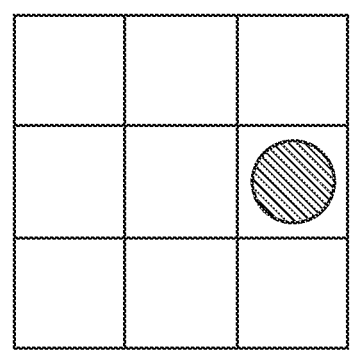

FIGS. 6A-6F show treatment spots representing the treatment laser being fired or delivered within the treatment boundaries or patterns or delivered coaxially therewith. The treatment spots may represent visible tissue damage that occurs when the treatment laser is fired, such as in traditional photocoagulation procedures, or may represent a location where the treatment laser is fired even though no tissue damage is visible, such as in short duration pulse procedures. FIG. 6A illustrates a plurality of treatment spots 612, which represents locations within treatment boundary 510 where the treatment laser (e.g., treatment laser 112) was or is to be fired. Similarly, FIG. 6B illustrates treatment spots 622 being fired within each treatment square or rectangle 522 of treatment pattern 520. FIG. 6C illustrates treatment spots 632 being fired substantially within a center of each geometric shape 532 of treatment pattern 530 and FIG. 6D illustrates treatment spots 642 being fired within a substantial center of each hexagonal shape 542 of treatment pattern 540. FIG. 6C illustrates embodiments where arcuate therapeutic treatments are provided and FIG. 6D illustrate embodiments where the treatment spots are more tightly or closely spaced. The treatment spots of FIG. 6D may overlap with treatment spots in adjacent rows and/or columns. FIGS. 6E and 6F illustrate treatment spots 652 and 662 being delivered substantially coaxially with respect to aiming spots 552 and 562 of treatment patterns 550 and 560 respectively. In another embodiment, larger circles 652 and 662 may represent the defined treatment patterns and smaller spots 552 and 562 may represent the therapeutic laser fired or delivered within a substantial center of each treatment pattern. Such embodiments illustrate that the defined treatment patterns or boundaries need not have adjacent geometric shapes that touch. Rather, some or all of the geometric shapes may be isolated from one or more adjacent geometric shapes.

Although FIGS. 6B-6D show a single treatment spot being delivered within each of the geometric shapes, in some embodiments multiple spots (e.g., 2, 3, 4, or more) may be delivered within one or more of the geometric shapes. Similarly, the number of treatment spots delivered within each geometric shape may be varied to provide additional therapeutic treatment flexibility.

FIG. 8 illustrates a treatment pattern or boundary 810 being positioned adjacent tissue 820 of the retina for which a therapeutic treatment is not desired. Treatment pattern 810 is positioned adjacent tissue 820 so that tissue 820 is outside of the treatment pattern or boundary. Tissue 820 may be sensitive tissue, a feature of the eye (e.g., fovea, macula, and the like), and/or any other tissue for which the therapeutic treatment is not desired. As described above, treatment pattern 810 may be projected or defined on the retina so that a physician or user may position an outer edge or periphery of treatment pattern 810 adjacent tissue 820. The projection or definition of treatment pattern 810 on the retina allows the physician or user to position the treatment pattern as close to or distant from tissue 820 as desired while ensuring that tissue 820 is not treated. As also shown in FIG. 8, the therapeutic treatment (i.e., treatment spots 830) is confined within treatment pattern 810 to ensure that tissue 820 does not receive the therapeutic treatment. The shape of treatment pattern 810 and/or parameters of treatment pattern 810 (e.g., spacing, radius, row or column number, and the like) may be changed to accommodate various features of the eye. For example, the semi-circular pattern of FIG. 5C may be used encircle a portion of tissue 820 or the fovea. Likewise, the honeycomb pattern of FIG. 5D may be used to tightly pack treatment spots within the treatment area.

Embodiments of Therapeutic Treatment Procedures

In some embodiments, the treatment laser may be fired substantially within a geometric center of each of the geometric shapes as is shown in FIGS. 6B-6D. The treatment spot size of the treatment laser incident on the retina may be substantially equivalent in size or slightly smaller than the geometric shape. Further, as previously described, the aiming laser may be switched off during firing of the treatment laser and the treatment laser may be switched off when the aiming beam defines or outlines the treatment boundary or pattern.

The therapeutic treatment pulses or doses (e.g., the spots shown in FIG. 6A-6D) may be delivered during a continuous scan of the treatment laser beam (or more appropriately an axis of the treatment laser beam) through the treatment boundary or pattern, or the treatment laser beam may be sequentially moved to each target site and the treatment laser fired while the treatment laser is temporarily stopped. Continuous scan procedures may be particularly useful for mircropulse procedures to minimize start and stop times associated with the treatment laser and thereby minimize an overall procedure time. The treatment laser beam (i.e., an axis of the treatment laser) may be continuously scanned row by row and/or column by column through the treatment boundary/pattern (e.g., similar to a raster scan pattern) until the treatment laser beam reaches a designated end point and/or scans the entire treatment boundary or pattern. The treatment laser may be sequentially or repeatedly fired for a defined duration during the continuous scan as the treatment laser nears each specified target site. The treatment laser beam may be repositioned at a starting point of the scan and the continuous scan and firing process may be repeated so that additional therapeutic treatment is provided to some or all of the previously treated retinal tissue (e.g., additional therapeutic treatment is provided at some or each target site). In another embodiment, the treatment laser may be stopped or paused at each treatment location and a treatment laser beam repeatedly fired at the treatment location until a sufficient treatment is provided.

In short duration pulse procedures, the interval between therapeutic treatment pulses or doses at the same target site may be sufficiently long so that the retinal tissue being treated sufficiently relaxes and a temperature of the tissue remains below a threshold of coagulative damage, thereby minimizing tissue damage. The thermal effect of the short duration pulse procedure may be confined only to the retinal pigment epithelial layer. In some embodiments, this relaxation interval, or thermal relaxation time delay, may be about 190 microseconds or longer. Likewise, in some embodiments, the firing duration of the treatment laser (i.e., the treatment pulse or dose duration) is between about 5 and 15 microsecond, and more commonly about 10 microseconds.

Each scan and firing process (i.e., between defined start and end points) may constitute a cycle of a short duration pulse procedure. The short duration pulse procedure may involve between about 10 and 10,000 cycles. In some embodiments, the treatments laser is fired at 9 or more treatment sites during each cycle of the scan and each short duration pulse cycle is completed in between about 0.5 and 1.5 milliseconds, and more commonly about 1 millisecond, although it should be realized that the treatment laser may be fired at any number of treatment sites and the each cycle may include a shorter or longer cycle duration. Further, a therapeutic treatment procedure for a given treatment boundary/pattern may involve a single continuous scan or several continuous scans each having different start and end points.

In an alternative embodiment, the treatment laser may be sequentially positioned at each target site and a series of short duration pulses may be delivered at that target site before moving to the next treatment site. Each pulse may be fired for a specified duration (e.g., between about 5 and 15 microsecond, and more commonly about 10 microseconds) and may have a sufficiently long relaxation interval (e.g., about 190 microseconds or longer) so that the retinal tissue at the treatment site sufficiently relaxes and a temperature of the tissue remains below a coagulation temperature, thereby minimizing tissue damage. The short duration pulses may be sufficient to induce or provide photoactivation of a therapeutic healing as is commonly known in short duration pulse procedures. The former short duration pulse embodiment provides the advantage of allowing the treatment laser to be fired at other treatment sites during the relaxation interval, thereby minimizing an overall treatment time.

The short duration pulse procedure may also include delivering the series of pulses as the treatment laser beam (i.e., the axis of the treatment laser) is continuously scanned with a specified time interval between each laser pulse or dose so as to provide a predetermined spacing between adjacent treatment spots. Such procedures may be beneficial when a treatment pattern having an array of geometric shapes, such as those shown in FIGS. 5B-5D is used and/or when an array of aiming spots, such as those shown in FIGS. 5E and 5F is used. The specified time interval and resulting spacing may be such that each pulse is delivered within one of the geometric shapes, substantially within a geometric center of each shape, and/or over one or more of the aiming spots.

A therapeutic treatment procedure may involve delivering therapeutic treatment to one area of the retina and then subsequently delivering therapeutic treatment to one or more other areas of the retina. For example, the aiming device (e.g., aiming device 130) may define a first treatment boundary or pattern on a first area of the retina and deliver therapeutic treatment within the defined first treatment boundary or pattern and then subsequently define a second treatment boundary or pattern (i.e., either the same or a different boundary/pattern) on a second area of the retina and deliver therapeutic treatment within the defined second treatment boundary or pattern. This process may be repeated as often as desired to provide the therapeutic treatment.

FIG. 9A illustrates an elongated treatment spot 900 resulting from firing the treatment laser during a continuous scan process. The treatment spot of the treatment laser corresponding to FIG. 9A may have a substantially circular cross section. The elongated spot may occur because the treatment laser is continually moving during the firing process. As such, even though the short duration pulse firing duration is short (e.g., approximately 10 microseconds), some elongation may occur due to the continuous movement of the treatment laser. To minimize the effects of the continuously moving treatment laser, the cross section of the treatment spot incident on the tissue may be oval or oblong in a direction orthogonal to the treatment laser path as shown in FIG. 9B. A shown in FIG. 9C, the oval or oblong treatment spot 910 may facilitate in producing more circular treatment spots 930 or incident light profiles on the retina as the treatment laser beam, or more appropriately the axis of the treatment laser beam, is scanned across the retina and the series of pulses delivered.

Embodiments of Retinal Mapping/Tracking

Figure 10A:
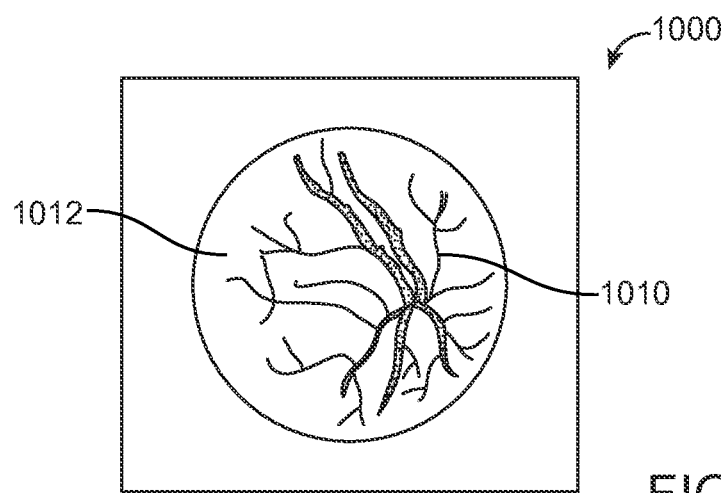
FIGS. 10A-10C illustrate a retinal image, profile, or map that may be used in a therapeutic treatment procedure.
Figure 10B:
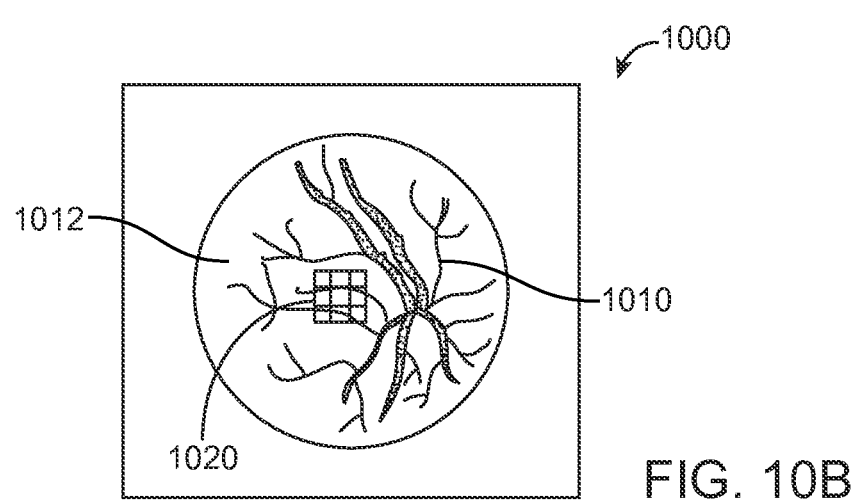
Figure 10C:
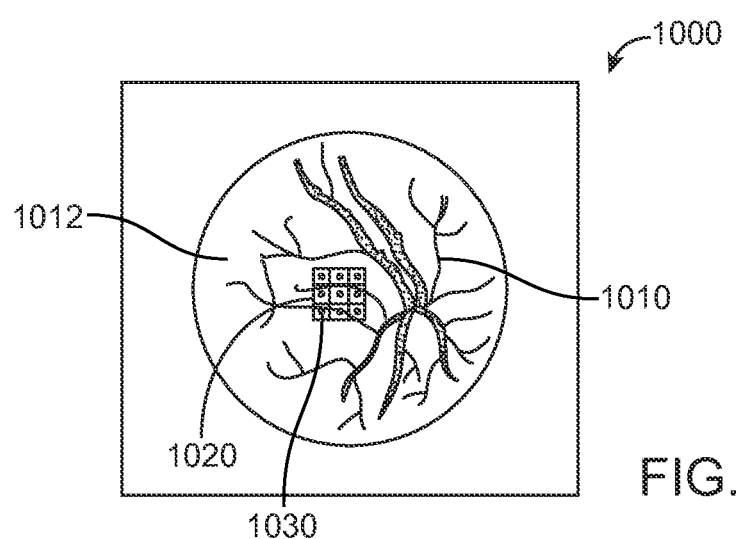

FIGS. 10A-10C illustrate embodiments involving retinal maps, profiles, or images that may be used in therapeutic treatment processes, such as those described herein. FIG. 10A shows a retinal map or image 1000 of a patient's retina that may be captured using one or more cameras (e.g., camera 360) of a slit lamp or other ophthalmic imaging instrument. As described above, computer system 330 may be communicatively coupled with camera 360 to provide retinal mapping, imaging, and/or tracking. Computer system 330 may have a measurement device capable of generating images 1000 of the retina 1012 and of providing information helpful for determining a treatment area or areas and/or treatment pattern or patterns to treat with the therapeutic treatment. A beam, such as treatment beam 112 may be directed toward a treatment area of the retina by referencing retinal image 1000. The beam may provide the therapeutic treatment. Indicia, such as treatment spots, may be superimposed on retinal image 1000 at a location corresponding to the treatment area to document or record the therapeutic treatment provided. For example, treatment spots or other indicia may be superimposed on retinal image 1000 at each location that the beam is fired. The plurality of superimposed treatments spots may display the therapeutic treatment provided. The beam may then be repositioned to another treatment area of the retina by referencing the retinal image and a second therapeutic treatment provided and/or documented with superimposed treatment spots in the manner described above.

In some embodiments, a treatment area, boundary, and/or pattern 1020 may be referenced to the image 1000, so that a relationship between the location of the treatment area, boundary, and/or pattern 1020 and the image 1000 data can be established. The treatment area, boundary, and/or pattern 1020 may be linked to a feature or reference location 1010 on the retina 1012, which can be identified in the image 1000, such as a various veins, arteries, the optic disc, macula, retinal landmarks or features, and the like. Along with locating and/or determining the treatment area, boundary, and/or pattern 1020, the measurement device (e.g., computer system 330) may also include at least a portion of a processor system capable of calculating a set of treatment instructions to be used by a therapeutic treatment deliver system, such as adapter 100 and slit lamp 200.

The measurement device (e.g., computer system 330) and/or therapeutic treatment system (e.g., adapter 100 and slit lamp 200) can have software stored in a memory and hardware that can be used to control the taking of images and delivery of therapeutic treatment (e.g., treatment laser 112) to the patient's retina, the location or the position (optionally including translations in the x, y, and z directions and torsional rotations) of the patient's eye relative to one or more optical axes of the imaging assemblies, and the like. In exemplary embodiments, among other functions, computer system 330 (e.g., the measurement device) can be programmed to calculate treatment areas, boundaries, and/or patterns 1020 based on the image(s) taken with camera 360, and measure the offset between the patient's eye in the two images. Additionally, computer system 330 can be programmed to measure, effectively in real-time, the movement or position x(t), y(t), z(t), and rotational orientation of the patient's eye/retina relative to the optical axis of the laser beam (e.g., treatment laser 112 and/or aiming laser 122) so as to allow computer system 330 to register or align the desired treatment areas, boundaries, and/or patterns 1020 on the real-time position of the patient's eye.

In order to register the desired treatment areas, boundaries, and/or patterns 1020 of the patient's eye during the treatment, the images from the patient's retina taken by the camera 360 should share a common coordinate system. The common coordinate system may be based a center of the pupil or inner iris boundary, a center of the outer iris boundary, a center of various veins or arteries, a center of the optic disc or macula, a center of other retinal landmarks or features, or any other suitable feature of the eye.

As shown in FIG. 10B, one or more desired areas to treat with the therapeutic treatment may be determined with reference to diagnostic data associated with a first retinal image 1000 that is captured by camera 360 and/or previously obtained and input into computer system 330. A treatment area, boundary, and/or pattern 1020 to use for each respective treatment area may then be determined. These determinations may be made by a physician with or without the aid of computer system 330, or, in some embodiments, may be made automatically by computer system 330. Each treatment area, boundary, and/or pattern 1020 may be the same or may vary.

In some embodiments, the one or more desired treatment areas, boundaries, and/or patterns 1020 may then be programmed into computer system 330. Computer system 330 may operate with camera 360 to determine an area of the patient's retina 1012 that corresponds to the programmed treatment area(s) by comparing the patient's retina and retinal image 1000. In some embodiments, a second image of the eye is captured by camera 360, such as immediately prior to the therapeutic treatment procedure, and the two images are processed or compared to generate retinal treatment location information, which information may then be referenced to the second image. The treatment area(s), boundary(s), and/or pattern(s) may be superimposed on the patient's retina and/or displayed on a display interface (e.g., touch screen display 320) prior to the therapeutic treatment procedure in order to display the treatment(s) that will be provided and the areas that will receive such treatment(s). A physician or user may evaluate the treatment(s) and, if desired, modify or adjust a property (e.g., orientation, scale, boundary, pattern, and the like) of one or more of the treatments.

In some embodiments, computer system 330 may instruct adapter 100, or some component of a therapeutic treatment system, to fire an aiming laser beam (e.g., aiming laser 122) onto the determined treatment area of retina 1012 to define the treatment boundary and/or pattern 1020 on retina 1012. In other embodiments, a treatment boundary and/or pattern may not be defined on the retina and, thus, an aiming laser may not be needed.

Computer system 330 may also instruct laser delivery instrument 310, or other therapeutic treatment system component, to direct a therapeutic laser beam (e.g., treatment laser 112) onto the retina 1012 within the treatment area and/or within the treatment boundary and/or pattern 1020 defined by the aiming laser beam. The second laser beam (e.g., treatment laser 112) may deliver the desired therapeutic treatment pulses or doses 1030 (e.g., short duration pulse or other treatment) to retinal tissue within the defined treatment area and/or treatment boundary and/or pattern 1020 as shown in FIG. 10C.

The retinal image 1000 may be stored in a memory device and/or database for immediate or future reference. As briefly described above, the therapeutic treatments 1030 provided on the retinal tissue 1012 may be documented or recorded on the retinal image 1000 in order to track the treatment or treatments the patient receives. Documenting/recording of the therapeutic treatments provided may involve monitoring a position of the treatment laser beam 112 (i.e., a position of the laser beam axis) with respect to retinal image 1000 and recording each position of the treatment laser beam when the treatment laser 112 is fired. Individual treatment spots or locations may be recorded on retinal image 1000 to display the areas that have received treatment. Such mapping and documenting/recording procedures may be particularly useful in short duration pulse treatment procedures where no visible effects of the therapeutic treatment are present and previous short duration pulse treatments may otherwise been unknown.

Similarly, a plurality of therapeutic treatments to provide to a patient over one or more treatment sessions may be mapped or imaged on retinal image 1000. Each therapeutic treatment subsequently provided may be documented or recorded on retinal image 1000, or a second retinal image, so that the actual therapeutic treatments provided may be compared with the therapeutic treatments mapped or imaged in order to track an overall treatment status of the patient or determine the progress of the treatments and the patient's response to such treatments.

Computer system 330 and camera 360 may also be used to adjust the therapeutic treatment system (e.g., treatment laser 112 and/or aiming laser 122) in response to movement of the patient's eye. For example, computer system 330 may reference retinal image 1000 with one or more other images provided by camera 360 to determine whether the patient's eye has moved. In response to movement of the eye, the position of the aiming laser 122 may be adjusted so that the projected or defined treatment boundary/pattern maintains a correct orientation with respect to the retina. Likewise, the position of the treatment laser 112 may also be adjusted to compensate for movement of the eye to ensure that the treatment laser 112 is fired within the adjusted treatment area, boundary, and/or pattern. The adjustment may include determining a new position of retinal features of the eye (e.g., veins, arteries, macula, and the like), determining a new position of the treatment boundary/pattern based on the new position of the retinal features, and adjusting the aiming device 130 accordingly. The images captured by camera 360 may be provided to computer system 330 and compared with retinal image 1000 in real time to provide real time tracking and adjustment of the therapeutic treatment based on movement of the eye.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method for treating an eye of a patient comprising:
    delivering a first beam from a first light source along a first path to an aiming device;
    delivering a second beam from a second light source along a second path to the aiming device, the second path being off-axis from the first path;
    projecting, via the aiming device, the first beam onto retinal tissue of the patient's eye;
    defining, via the first beam, a boundary on the retinal tissue separating the retinal tissue to a first area and a second area, the boundary including a plurality of continuous and connected geometric shapes; and
    delivering, via the second beam, a therapeutic treatment to the retinal tissue of the patient's eye by selectively directing the second beam onto the retinal tissue of the patient's eye within the first area;
    wherein the first beam is switched off during firing of the second beam and the second beam is switch off during firing of the first beam, and wherein the first beam is switched on between subsequent firings of the second beam to redefine the boundary on the retinal tissue between subsequent firings of the second beam, the first beam being projected onto the retinal tissue so that a resulting visual effect is a continuous solid boundary of the continuous and connected geometric shapes on the retinal tissue.

2. The method of claim 1, further comprising:
    positioning the boundary adjacent an identified region of the patient's eye so that the identified region is within the second area, the identified region including tissue that is not to be treated with the treatment; and
    directing the second beam within the first area so as to avoid delivering the therapeutic treatment to the tissue of the identified region.

3. The method of claim 1, each geometric shape defines an area within which the second beam is directed to deliver the treatment, the second beam being directed within each of the geometric shapes.

4. The method of claim 3, wherein the first beam outlines the plurality of continuous and connected geometric shapes on the retinal tissue.

5. The method of claim 4, wherein the location of the first beam is adjusted between each of a plurality of pulses.

6. The method of claim 3, wherein the geometric shapes comprises one or more of the following:
    a grid having a plurality of squares;
    a grid having a plurality of rectangles;
    a semicircle pattern,
    a pattern of circles, and
    a hexagonal pattern.

7. The method of claim 3, further comprising directing the second beam over a geometric center of each of the geometric shapes.

8. The method of claim 7, wherein a spot of the second beam incident on the retinal tissue is entirely within a periphery of the geometric shape formed by the first beam.

9. The method of claim 1, further comprising delivering a plurality of pulses of the second beam within the boundary to provide the treatment.

10. The method of claim 1, further comprising adjusting either or both a scale of the boundary and an orientation of the boundary.

11. The method of claim 1, wherein defining the boundary comprises directing the first beam along a periphery of the boundary.

12. The method of claim 11, wherein the first beam has a visible spot size on the retina that is smaller than a spot size of the second beam.

13. The method of claim 1, wherein delivering the therapeutic treatment comprises causing photocoagulation of the retinal tissue.

14. The method of claim 1, further comprising delivering the second beam in a series of pulses of sufficiently short duration so as to avoid inducing traditional photocoagulation of the retinal tissue while inducing photoactivation of a therapeutic healing response.

15. A method for providing therapeutic treatment to a patient's eye, the method comprising:
    defining, via an aiming beam, a treatment pattern onto a retina of the patient's eye, the treatment pattern defining a first area of retinal tissue and a second area of retinal tissue, the treatment pattern comprising a plurality of geometric shapes within the first area; and
    delivering, via a treatment beam, a therapeutic treatment to retinal tissue of the first area by selectively directing the treatment beam within an interior region of each geometric shape of the plurality of geometric shapes, the treatment beam being delivered along a path that is different than a path of the aiming beam;
    wherein the aiming beam is switched off during firing of the treatment beam and is switched on between subsequent firings of the treatment beam to redefine the treatment pattern on the retinal tissue resulting in a continuous appearance of the geometric shapes being provided on the retinal tissue.

16. The method of claim 15, wherein the treatment beam is sequentially directed within each of the geometric shapes.

17. The method of claim 16, wherein the treatment pattern comprises a grid having a plurality of rows and columns, and wherein the treatment beam is sequentially scanned along the plurality of rows and columns to deliver the treatment beam to the retinal tissue.

18. The method of claim 17, wherein the grid comprises an M×N array of squares or rectangles arranged in a linear or semicircular pattern.

19. The method of claim 15, further comprising:
- defining a second treatment pattern onto the retina at a location that has not received the treatment, the second treatment pattern defining a third area of retinal tissue and a fourth area of retinal tissue; and
- delivering, via the treatment beam, the therapeutic treatment to retinal tissue of the third area by selectively directing the treatment beam within the third area.

* * * * *